United States Patent [19]

Leung et al.

[11] Patent Number: 5,010,301

[45] Date of Patent: * Apr. 23, 1991

[54] METHOD FOR DETERMINING THE SWELLING CLAY CONTENT OF CEMENT MIXTURES BY DIELECTRIC MEASUREMENTS

[75] Inventors: Peter K. Leung, Sugar Land; Ronald P. Steiger; Kenneth R. Kunze, both of Houston, all of Tex.

[73] Assignee: Exxon Production Research Company, Houston, Tex.

[*] Notice: The portion of the term of this patent subsequent to Oct. 24, 2006 has been disclaimed.

[21] Appl. No.: 397,053

[22] Filed: Aug. 22, 1989

[51] Int. Cl.$^5$ .......................... G01V 3/06; G01V 3/12
[52] U.S. Cl. ........................................ 324/376; 73/153
[58] Field of Search ............... 324/341, 351, 376, 377; 73/151-153

[56] References Cited

U.S. PATENT DOCUMENTS

| | | | |
|---|---|---|---|
| 2,802,172 | 8/1957 | Mueller et al. | 324/376 |
| 3,302,161 | 1/1967 | Glanville | 324/376 |
| 3,617,868 | 11/1971 | Beitel et al. | 324/376 |
| 3,982,177 | 9/1976 | Walker et al. | 324/376 |
| 4,410,052 | 10/1983 | Mamadzhanov et al. | 324/351 X |
| 4,608,859 | 9/1986 | Rockley | 73/153 |
| 4,644,283 | 2/1987 | Vinegar et al. | 324/376 |
| 4,652,829 | 3/1987 | Safinya | 324/341 X |
| 4,734,649 | 3/1988 | Barnaby | 324/376 |
| 4,769,606 | 9/1988 | Vinegar et al. | 324/376 |
| 4,876,512 | 10/1989 | Kroejev et al. | 324/376 |

OTHER PUBLICATIONS

Brindley, G. W. and Brown, G., editors, "Crystal Structures of Clay Minerals and their X-Ray Identification", Mineralogical Society, London, 1980, Chapter 5.
Van Olphen, H., "An Introduction to Clay Colloid Chemistry", Wiley-Interscience, New York, 1977, Chapter 5.
American Petroleum Institute Publication RP 13B, "API Recommended Practice Standard Procedure for Field Testing Drilling Fluids", Eleventh Edition, May 1, 1985, pp. 17 and 18.
Theng, B. K. G., "The Chemistry of Clay-Organic Reactions", John Wiley & Sons, New York, 1974, Chapter 3.
Jaynes, W. F. and Bigham, J. M., "Multiple Cation-Exchange Capacity Measurements on Standard Clays Using a Commercial Mechanical Extractor", Clays and Minerals, 1986, vol. 34, No. 1, pp. 93-98.
Raythatha, R. and Sen, P. N., "Dielectric Properties of Clay Suspensions in the MHz to GHz Range", Journal of Colloid and Interface Science, Feb. 1986, vol. 109, No. 2, pp. 301-309.
Shen, L. C., "Problems in Dielectric-Constant Logging and Possible Routes to their Solutions", The Log Analyst, 1985, Nov.-Dec., pp. 14-25.
Wharton, R. P. et al., "Electromagnetic Propagation Logging: Advances in Technique and Interpretation", 55th Ann. Fall Tech. Conf., Dallas, Tex., Sep. 21-24, 1980, SPE Paper 9267.
Lockhart, N. C., "Electrical Properties and the Surface Characteristics and Structure of Clays", Journal of Colloid and Interface Science, 1980, vol. 74, No. 2, pp. 509-519.
Weiler, R. A. and Chaussidon, J., "Surface Conductivity and Dielectric Properties of Montmorillonite Gels", Clay and Minerals, 1968, vol. 16, pp. 147-155.

Primary Examiner—Reinhard J. Eisenzopf
Assistant Examiner—Warren S. Edmonds
Attorney, Agent, or Firm—Raul R. Montes

[57] ABSTRACT

A method for determining at wellsites the swelling-clay content of cement mixtures by high-frequency dielectric measurements including: grinding a cement mix sample to a size suitable for testing; washing the cement mix sample with a fluid having a water activity substantially less than water, which may contain a soluble cation; packing the washed cement mix sample into a sample cell suitable for dielectric measurement; measuring the dielectric constant at a preselected frequency; and comparing the measured dielectric constant of the cement mix sample to calibration curves.

21 Claims, 2 Drawing Sheets

METHOD FOR DETERMINING THE SWELLING CLAY CONTENT OF CEMENT MIXTURES BY DIELECTRIC MEASUREMENTS

FIELD OF THE INVENTION

This invention pertains to a method for determining the swelling-clay content of cement mixtures by high-frequency dielectric constant measurements.

BACKGROUND OF THE INVENTION

The determination of the swelling-clay content, especially smectite content, of cement mixtures (also referred to as "cement mix") is important in the design and evaluation of cement slurry formulations for use in the exploration for and the production of hydrocarbons. The cement setting process is a chemical reaction, and the chemical environment, including the swelling-clay content of the cement slurry, will affect the behavior of the cement slurry and will affect the properties of the cured cement. Parameters such as wellbore fluids and reservoir characteristics such as formation types and formation fluids will influence the slurry design and operation during cementing.

Bentonite (a smectite clay, also commonly referred to as "gel" in oilfield terminology) is a swelling clay which is often added to cement mixtures to decrease the slurry density, but it can significantly reduce the cement strength if excessive amounts are used. Bentonite can also enter the cement slurry during drilling fluid displacement, and it is often desirable to analyze return cement from failed cement jobs to assess this possibility.

Drilling fluid removal is a critical step in the cementing process. A successful cement job requires that all the cement be bonded to the casing and to the formation. This bonding requires that the drilling fluid ("drilling mud" or just "mud") that previously occupied that space in the wellbore be completely displaced by special preflushes and/or the cement slurry. Failure to remove all the mud may result in channels of mud along the length of the pipe or borehole. Because mud has no bonding strength and is easily flocculated by formation fluids, channels result in a poor cement job. Also, channels within the set cement may allow undesired migration of well fluids into or out of the formation. Migration of hydrocarbons from a high pressure zone to other zones can result in economic loss. Also, a poor cement job can result in poor confinement of stimulation treatments. Acidizing or hydraulically fracturing a zone that is not isolated by a competent cement sheath can result in the loss of treating fluids into undesirable zones. Breaking out of the productive zone limits the penetration by the treating fluid and may irreparably destroy the natural confining barriers.

Also, failure to displace mud ahead of the cement may lead to severe contamination of the cement with swellable clay and drill solids. This contamination causes weakening of the cement. As mentioned earlier, severe contamination may also occur if excessive amounts of swelling clay (e.g. bentonite) are added to reduce the density of the slurry.

Contamination of cement by swellable clays, either from mud contamination or excess bentonite addition, results in poor quality set cement. The result can vary from production of unwanted fluids to attack on the casing by corrosive waters. A poor cement job may also result in insufficient cement strength to support casing which in turn may result in casing movement, loss of casing integrity, and inability to support well control equipment.

It is desirable, therefore, to be able to obtain, at the wellsite, timely estimates of the swelling-clay content of cement mixtures, both before the cement is used and in cured samples that may be obtained from the subsurface.

Two of the most common methods for determining the swelling-clay content of a sample are the X-ray diffraction method and the cation exchange capacity (CEC) method. Both of these methods are well established in the art. Briefly, the X-ray diffraction method provides semi-quantitative mineral contents. See for example, "Crystal Structures of Clay Minerals and their X-ray Identification", edited by G. W. Brindley and G. Brown, Mineralogical Society, 1980, London, Chapter 5, for a brief summary of the X-ray diffraction method used in determining swelling-clay content. The CEC method, on the other hand, correlates the number of exchangeable cations in a sample (cations in the sample that can be replaced by another cation such as barium or ammonium) to the swelling-clay content. See for example, Van Olphen, H., "An Introduction to Clay Colloid Chemistry", Wiley-Interscience, New York, 1977, Chapter 5, and American Petroleum Institute publication RP 13B, "Recomended Practice for Standard Procedure in Testing Drilling Fluids", for brief summaries of CEC methods used in determining swelling-clay content.

However, it is also well established that the X-ray diffraction method usually requires days to complete and has to be performed in the lab. Furthermore, the X-ray diffraction method requires a sedimented, oriented deposit of clay crystals for quantitative results. Swelling clay particles that are part of cured (set) cement will not orient properly during the sedimentation process. The CEC method requires significant care in running the test and is not particularly suitable for wellsite use. In addition, the CEC method will not work for samples of set cement because of interference by the cement and alteration of the clay. Thus, neither of these methods are suitable for measuring swelling-clay content of cement mixtures, especially when the cement is cured.

There exists a need, therefore, for a rapid and reliable wellsite method for the determination of the swelling-clay content in cement mixtures.

Most recently, U.S. Ser. No. 175,081 to Kroeger et al. discloses a method for determining at wellsites the swelling-clay content of shales and shaly sandstone earth formations by dielectric measurements. Kroeger et al.'s method includes washing a sample of an earth formation with a fluid having a water activity substantially less than that of water, which fluid may contain a soluble cation, measuring the sample's dielectric constant at a preselected frequency, and comparing the results of this measurement to calibration curves to obtain a measurement of the swelling-clay content of the formation. Kroeger et al.'s method describes different levels of determinations depending on the nature of the formation samples.

Dielectric measurements are also utilized for other, unrelated purposes. For example, dielectric measurements are utilized in logging tools for making determinations of the water and hydrocarbon content in sandstones and carbonates. These logging tools are not designed for making swelling-clay content determinations.

In addition, these logging tools lose their effectiveness in high-salinity formations.

To the best of Applicants' knowledge, dielectric measurements are not used for making determinations of swelling-clay content of cement mixtures. In fact, excluding U.S. Ser. No. 175,081 to Kroeger et al., prior art actually dismisses dielectric responses observed between 1-50 MHz in dilute aqueous swelling-clay suspensions as anomalies which vanish with increasing salinity. See for example, Raythatha, R. and Sen, P. N., "Dielectric Properties of Clay Suspensions in the MHz to GHz Range", *Journal of Colloid and Interface Science*, Feb. 1986, Vol. 109, No. 2, in general, and particularly see pages 305 and 308 wherein it is stated that the electrochemical effects (of swelling-clays) become unimportant at high salinities and the geometrical effects dominate.

SUMMARY OF THE INVENTION

The present invention presents a method for rapidly determining at the wellsite the swelling-clay content in cement mixtures The invention describes a method for determining the swelling-clay content of wet and set cement mixtures by high-frequency dielectric measurements (for purposes of this application frequencies greater than 0.1 MHz are deemed "high frequency") which includes: grinding a dried cement mix sample to a size suitable for testing (preferably, the sample should be able to pass sieve sizes from 0.01 to 1.00 millimeter); washing the cement mix sample with a fluid having a water activity substantially less than that of water (using the dielectric constant as a measure of water activity, the dielectric constant of the fluid should be between 5 and 80) and which may contain a soluble cation (the soluble cations that may be added comprise: $Li^+$, $Na^+$, $K^+$, $Rb^+$, $Cs^+$, $(NH_4)^+$, $Mg^{+2}$, $Ca^{+2}$, $Ba^{+2}$, $Sr^{+2}$, $Co^{+2}$, $Ni^{+2}$, $Cu^{+2}$, $Zn^{+2}$, $La^{+3}$, $Fe^{+3}$, $Cr^{+3}$, $Al^{+3}$, or other similar cations); packing the washed cement mix sample into a sample cell suitable for dielectric measurement; measuring the dielectric constant at a preselected frequency to allow uniform comparison of cement mix samples (the frequency should be between 0.1 and 100 MHz); and comparing the measured dielectric constant of the cement mix sample to the measured dielectric constant of pure cement and pure swelling clay samples to obtain the amount of swelling clay in a particular cement mix. It is noted however that when the original cement mix sample consists of wet cement the grinding step described above is not necessary.

One important factor that makes the dielectric method applicable to cement mixtures is that the dielectric constants of swelling clays and cement are significantly different. Usually, swelling clays have a very high dielectric constant, varying from about 120 to 200; while the dielectric constant of cement is usually in the range of about 20-40.

It is an advantage of this invention that it can determine at wellsites in a timely manner the swelling-clay content of a cement mixture, either unset or set and cured.

Previously, there was no method available to measure swelling-clay content in a cured cement sample.

DETAILED DESCRIPTION OF THE PREFERRED EMBODIMENT

Figure 1:
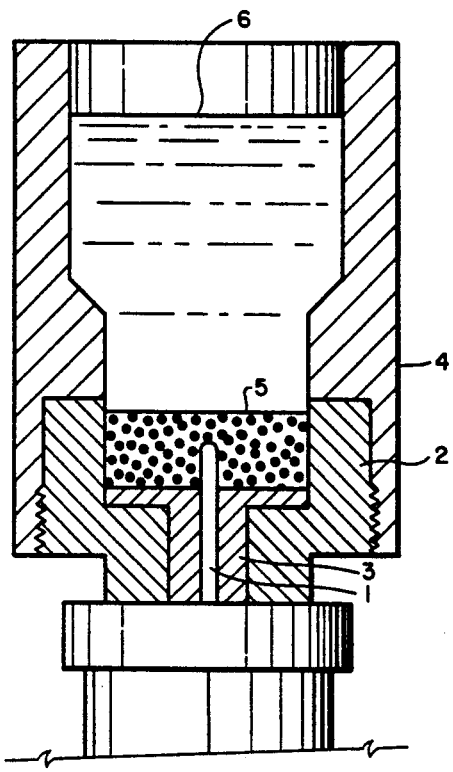
FIG. 1 schematically illustrates a sample cell suitable for dielectric constant measurements in connection with this invention.

The present invention concerns a timely wellsite method for determining the swelling-clay content of wet and set (dried, cured) cement mixtures. The principal steps in the preferred embodiment of this method include: grinding a dried cement mix sample to a predetermined size suitable for testing to allow uniform comparison of cement mix samples (this step however is not necessary for samples of wet, or unset cement); washing the cement mix sample with a fluid, which may contain a soluble cation, having a water activity substantially less than that of water; packing the washed cement mix sample into a sample cell suitable for dielectric measurements; measuring the dielectric constant at a preselected frequency to allow uniform comparison of cement mix samples, and comparing the measured dielectric constant of the cement mix sample to a calibration curve derived from samples of known swelling-clay content whose dielectric constants have been determined in substantially the same manner.

As mentioned earlier, one important factor that makes the dielectric method applicable to cement mixtures is that the dielectric constants of swelling clays and cement are significantly different. Usually, swelling clays have a very high dielectric constant, varying most often from 140 to 180; while the dielectric constant of cement is usually most often in the range of 25-35. Table 1 illustrates the typical range of dielectric constant measurements for pure cement and pure swelling clay.

TABLE 1

| Typical Dielectric Constant Measurements (DCM) | | |
|---|---|---|
| | Pure Cement | Pure Swelling Clay |
| DCM | 20-40 | 120-200 |

The invention will now be described in greater detail with reference to the accompanying drawings.

A cement mix sample is dried sufficiently so that it can be ground to a predetermined size. This size is neither so small that there is difficulty grinding high swelling-clay content samples nor so large that there is difficulty packing the sample in a measuring cell. For practical field testings, the sample should pass sieve sizes ranging from about 0.01 millimeter to 1.0 millimeter. A preferred sieve size is 0.12 millimeter because this size is a standard sieve size which is available with commonly available grinders. It is noted however that where the original cement mix sample is wet the drying and grinding steps described above are not necessary.

The cement mix sample is then washed with a fluid having a water activity substantially less than that of water. Using the dielectric constant as a measure of water activity, the fluid's dielectric constant should range between about 5 and 80. This fluid attenuates the swelling behavior of cement mix samples containing large amounts of swelling clays such that it will permit subsequent sample treatment and measurement. A fluid suitable for this purpose is an alcohol-water mixture. A suitable alcohol-water mixture which is commonly available is rubbing alcohol (70% isopropyl alcohol and 30% water by volume). The dielectric constant of this alcohol-water mixture is about 35, which corresponds to a suitable water activity level.

In a typical measuring routine, 200 milligrams of a dried, ground cement mix sample or approximately 300 milligrams of a wet cement sample are placed in a standard 7 milliliter test tube. The test tube is nearly filled with the fluid (for example, the alcohol-water mixture). The sample and fluid are then agitated or "vortexed" to provide satisfactory mixing of the fluid and sample. The test tube is then allowed to sit for a period suitable for the solvation, or hydration, of the swelling clay. This period of time may vary with experimental techniques. However, all samples which will be compared should sit for approximately the same period of time. In our experience, a period of about two hours will provide sufficient time for the solvation, or hydration, of the swelling clay. Ultimately, the washing step with the alcohol-water mixture should permit the solvation, or hydration, of even the least-swelling clays, such as kaolinite, as well as allow the subsequent centrifuging (at a relatively low rate without making necessary the addition of salts to promote flocculation) of the greatest swelling clays, such as bentonite.

The second level of determination requires that the sample be washed with a fluid to which sodium chloride has been added. A preferred concentration is 31.7 grams of sodium chloride per liter of fluid. Sodium cations are exchanged with all exchangeable cations in the sample and place all swelling clays in their most swellable state. Naturally occurring swelling clays, such as montmorillonite, may contain either sodium, calcium, potassium, or magnesium as exchangeable cations, or any combination of the four. The sodium exchange therefore standardizes the samples from different sites. This example utilizes sodium as the exchangeable cation. However, it is emphasized that other cations may be utilized in place of sodium to standardize the interlayer cation. Such other cations are: $Li^+$, $K^+$, $Rb^+$, $Cs^+$, $(NH_4)^+$, $Mg^{+2}$, $Ca^{+2}$, $Ba^{+2}$, $Sr^{+2}$, $Co^{+2}$, $Ni^{+2}$, $Cu^{+2}$, $Zn^{+2}$, $La^{+3}$, $Fe^{+3}$, $Cr^{+3}$, $Al^{+3}$. For this level of determination non-swelling state cations as well as swelling-state cations may be utilized.

Samples which have been washed with cation-containing fluids, for example sodium chloride, lanthanum chloride, or potassium chloride, are then washed with the non-cation-containing fluid, such as the rubbing alcohol, until the conductivity of the decantate is no more than twice that of the washing fluid in its original state (without the addition of salts). This level of conductivity represents the effective removal of excess exchanged cations from the washing fluid.

Subsequent to the washing step, the sample is packed into a sample cell suitable for dielectric constant measurements, such as the sample cell illustrated in FIG. 1. The use of coaxial sample cells for dielectric measurements at frequencies above 0.1 MHz are well established in the art. The coaxial design for the sample cell is used because of the ease of adding the slurry to the cell and because of the ease of packing the sample into the cell around the inner coaxial conductor by centrifuge methods. As shown in FIG. 1, a suitable sample cell is of a coaxial geometry, consisting of a center conductor 1 and an outer conductor 2 separated by a teflon spacer 3. A plastic jacket 4 has been attached to the outer conductor 2. The cement mix sample 5 and fluid 6 are added to the cavity of the sample cell. When the cement mix sample 5 has been packed into the sample cell, the cement mix sample 5 resides between the center conductor 1 and outer conductor 2, above the teflon spacer 3, and completely covers the center conductor 1. The fluid 6 is contained above the cement mix sample 5 and is contained within the plastic jacket 4.

In order to transfer the washed sample to this sample cell, portions of the non-cation-containing fluid are added to the sample. The sample and fluid are vortexed to provide satisfactory mixing, and the slurry is transferred into the sample cell.

The slurry-filled sample cell is then centrifuged for packing the sample in the sample cell. For example, centrifuging the sample at a rate of 1800 revolutions per minute for one minute uniformly packs the sample between the inner and outer conductors of the coaxial sample cell leaving the fluid in the plastic jacket above the measuring portion of the sample cell. This centrifuging rate is suggested because it is a moderate rate for small, portable centrifuges and because the rate and duration are sufficient to adequately pack the swelling clay into the sample cell.

The sample cell is then attached to a capacitance meter operating at a set frequency. Capacitance meters are well known in the art and are commonly available. A suitable test frequency is 1 MHz. A frequency of 1 MHz is sufficiently high to avoid electrode-polarization effects which distort measurements at lower frequencies and is sufficiently low to quantify the magnitude of the swelling-clay dielectric response. This dielectric response originates within the interlayer region of the swelling clay. This response occurs due to the reduced mobility of the interlayer exchangeable cations (for example, $Na^+$ or $La^{+3}$).

The sample's capacitance is measured and converted to the dielectric constant by well established methods. Briefly, the capacitances of two standards placed in the cell may be measured (for example, air whose dielectric constant is 1 and distilled water whose dielectric constant is .78 at a temperature of 25° C.). A linear relationship may then be established between the measured capacitance and the dielectric constant.

Comparisons to other samples of known dielectric constant and swelling-clay content are made to determine the swelling-clay content of the sample being tested.

The duration of the entire measurement process, including washing and testing, takes about 30 minutes.

Using the above test procedures, the dielectric constant of the cement mix ($DCM_{cement\ mix}$) can be measured. To identify the amount of swelling clay added in the cement mix, the following equation may be used:

$$DCM_{cement\ mix} = a\ DCM_{pure\ swelling\ clay} + (1-a) DCM_{pure\ cement} \quad (1)$$

where:
a is the amount of swelling clay in the cement mix in a fraction of total weight;
$DCM_{pure\ cement}$ is the dielectric constant of pure cement.
  In general, this dielectric constant measurement is very low, ranging from 20 to 40;

DCM$_{pure\ swelling\ clay}$ is the dielectric constant of swelling clay type of material. The dielectric constant measurement of swelling clays is high, varying from 120 to 200.

Equation 1 can be rearranged to determine the amount of swelling clay in a fraction of total cement weight:

$$a = \frac{(DCM_{cement\ mix} - DCM_{pure\ cement})}{(DCM_{pure\ swelling\ clay} - DCM_{pure\ cement})} \quad (2)$$

Figure 2:
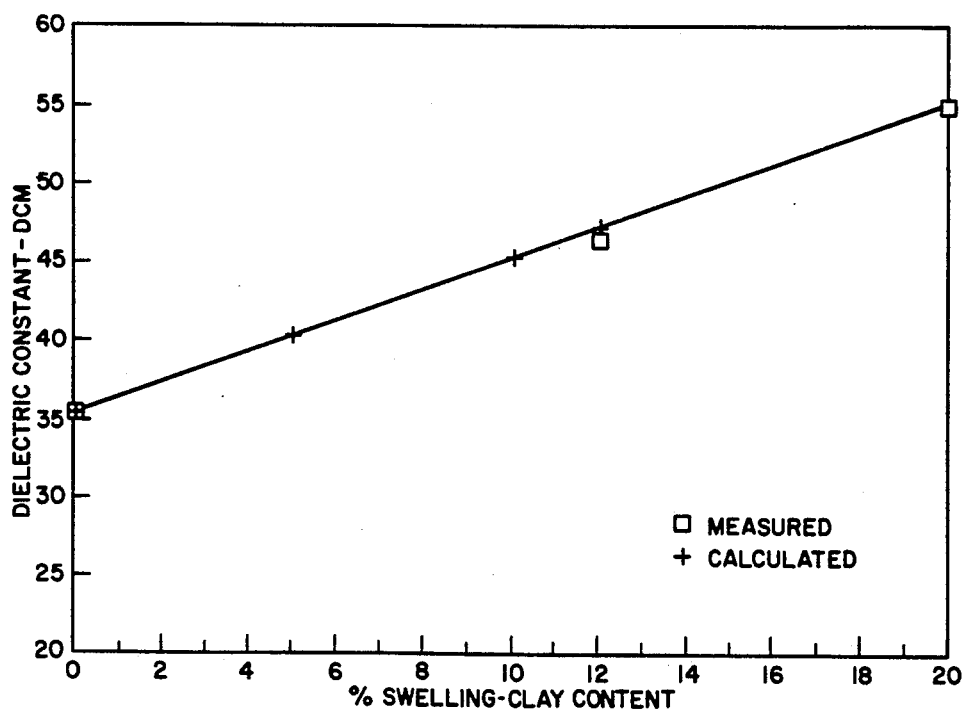
FIG. 2 illustrates a comparison of the measured and the calculated dielectric constants of cement mix samples with the known percent swelling-clay content of the cement mix samples.

An experiment was conducted to validate the described method. Three cement samples were formulated using Class H Portland cement These samples contained 0, 12, and 20% swelling-clay content, respectively. The swelling clay material used was Wyoming bentonite processed and packed by Magcobar. The samples were cured under 3000 psi (20,684.3 kPa) confining pressure at 150° F. (65.5° C.). Then, the dielectric constant for each sample was measured using the above procedures. It was observed that the dielectric constant increased with increasing amount of swelling-clay content in the cement. It was also found that the calculated dielectric constants (using Equation 1) were in good agreement with the measured values. The attached FIG. 2 illustrates the comparison of the calculated values with the measurements. The good agreement between the measured and calculated values suggests that the dielectric method should be a reliable technique to measure amount of bentonite added into the cement.

Figure 3:
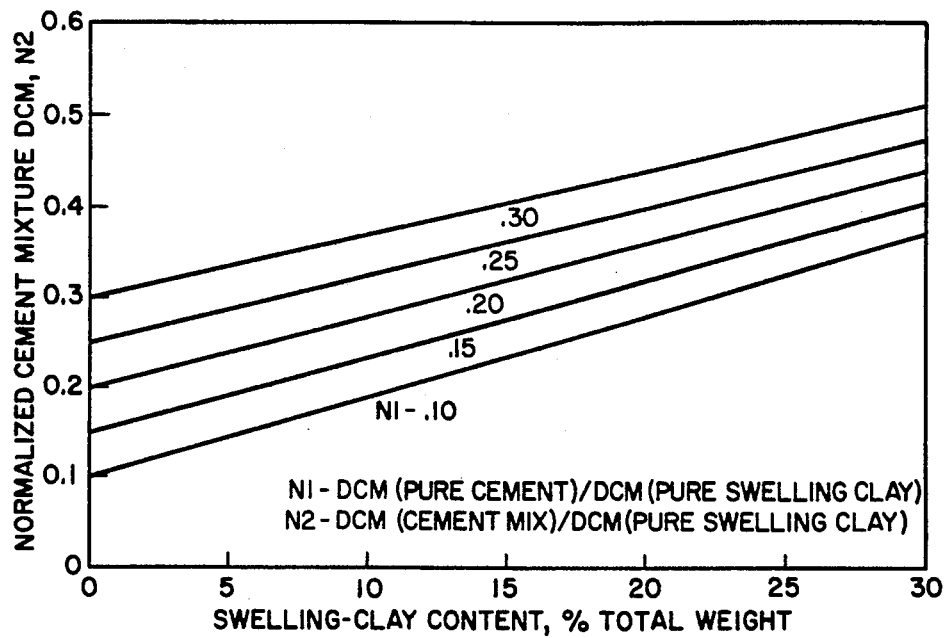
FIG. 3 is a percent swelling-clay content versus dielectric constant diagram for a typical cement mixture showing the correlation between the dielectric constant and the percent swelling-clay content.
Figure 4:
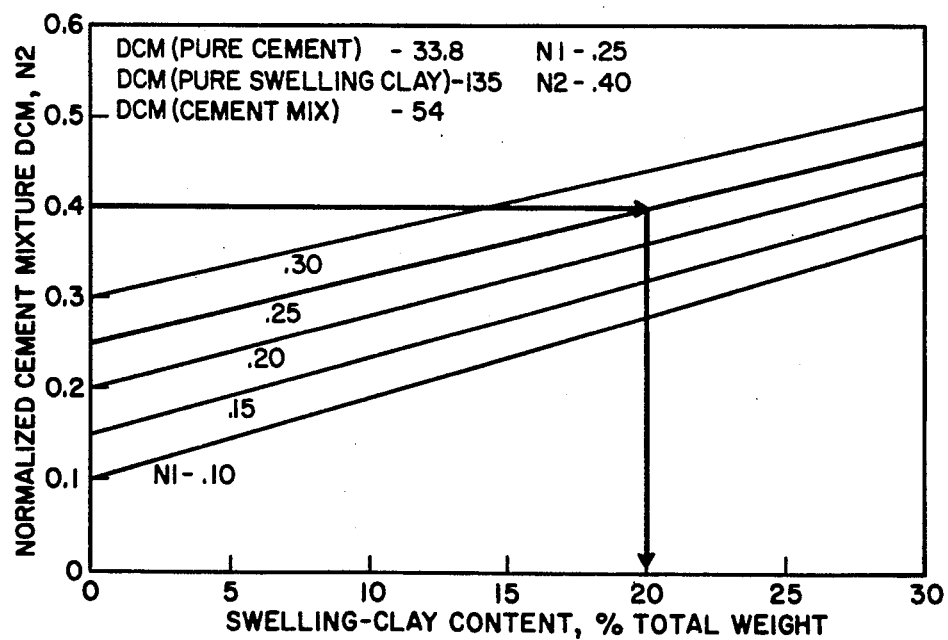
FIG. 4 is an example of how to determine the percent swelling-clay content from the correlation chart presented in FIG. 2.

In addition to Equation 2, the swelling-clay content of a cement mix can also be determined by using a set of calibration curves as shown in FIG. 3. This Figure shows two dimensionless parameters, N1 and N2. N1 is the ratio of dielectric constants between pure cement and pure swelling clay and N2 is the dielectric constant ratio between cement mix and pure swelling clay. FIG. 4 demonstrates how to obtain swelling-clay content measurements from this set of curves. In this example, the dielectric constants for pure cement, pure swelling clay, and cement mix are 33.8, 135, and 54, respectively. The corresponding values for N1 and N2 are 0.25 and 0.40. With these two parameters, the swelling-clay content is determined to be 20% of the total solids in the cement mix.

It is emphasized that FIGS. 3 through 4 are merely examples of the correlations which may be obtained to determine the swelling-clay content of formations using the invention. It is to be understood that many other similar correlations and diagrams may be created using the invention to obtain the swelling-clay content of samples.

The above description and examples of the invention are offered only for the purpose of illustration, and it is not intended that the invention be limited except by the scope of the appended claims.

We claim:

1. A method for measuring the swelling-clay content of wet cement mixtures by dielectric measurements, comprising the steps of:
   (a) washing a wet cement mix sample with a fluid having a water activity substantially less than that of water;
   (b) packing the washed cement mix sample into a sample cell suitable for dielectric measurement;
   (c) measuring the dielectric constant at a preselected frequency; and
   (d) comparing the measured dielectric constant of the cement mix sample to a calibration curve to determine the swelling-clay content.

2. A method for measuring the swelling-clay content of cement mixtures by dielectric measurements, comprising the steps of:
   (a) grinding a cement mix sample to a size suitable for testing;
   (b) washing the cement mix sample with a fluid having a water activity substantially less than that of water;
   (c) packing the washed cement mix sample into a sample cell suitable for dielectric measurement;
   (d) measuring the dielectric constant at a preselected frequency; and
   (e) comparing the measured dielectric constant of the cement mix sample to a calibration curve to determine the swelling-clay content.

3. The method of claim 1 or 2 further including the step of repeating steps a through e for each sample to be compared.

4. The method of claim 1 or 2 wherein said fluid is a mixture of alcohol and water.

5. The method of claim 1 or 2 wherein said fluid is a mixture of 70% (volume) isopropyl alcohol and 30% (volume) water.

6. The method of claim 1 or 2 wherein said packing is accomplished by centrifuging the sample cell.

7. The method of claim 1 or 2 wherein the preselected frequency of measurement is about 1 megahertz.

8. A method for measuring the swelling-clay content of cement mixtures by high-frequency dielectric measurements, comprising the steps of:
   (a) grinding a cement mix sample to a predetermined size suitable for testing;
   (b) washing the cement mix sample with a fluid having a water activity substantially less than that of water;
   (c) packing the washed cement mix sample into a sample cell suitable for dielectric measurement;
   (d) measuring the dielectric constant at a preselected frequency to allow uniform comparison of cement mix samples; and
   (e) repeating steps a through d for a sample of pure swellable clay;
   (f) repeating steps a through d for a sample of pure cement;
   (g) obtaining the swelling-clay content of the cement mix in accordance with the following relationship:

$$a = \frac{DCM_{cement\ mix} - DCM_{pure\ cement}}{DCM_{pure\ swelling\ clay} - DCM_{pure\ cement}}$$

where:
   DCM$_{cement\ mix}$ is the measured dielectric constant of the cement mix sample;
   DCM$_{pure\ cement}$ is the measured dielectric constant of the pure cement sample;
   DCM$_{pure\ swellable\ clay}$ is the measured dielectric constant of te pure swellable clay sample; and
   a is the amount swelling-clay content in the cement mix in a fraction of total weight.

9. The method of claim 8, further including the step of repeating steps a through g for each sample to be compared.

10. The method of claim 8 wherein said fluid is a mixture of alcohol and water.

11. The method of claim 10 wherein said mixture is 70% (volume) isopropyl alcohol and 30% (volume) water.

12. The method of claim 8 wherein said packing is accomplished by centrifuging the sample cell.

13. The method of claim 8 wherein the preselected frequency of measurement is about 1 megahertz.

14. A method for measuring the swelling-clay content of cement mixtures by high-frequency dielectric measurements, comprising the steps of:
(a) grinding a dried cement mix sample to a predetermined size suitable for testing;
(b) washing the cement mix sample with a fluid having a water activity substantially less than that of water to which a cation has been added;
(c) packing the washed cement mix sample into a sample cell suitable for dielectric measurement;
(d) measuring the dielectric constant at a preselected frequency to allow uniform comparison of cement mix samples; and
(e) comparing the measured dielectric constant of the cement mix sample to a calibration curve derived from samples of known dielectric constant and swelling-clay content.

15. The method of claim 14 wherein said cation comprises $Li^+$, $Na^+$, $K^+$, $Rb^+$, $Cs^+$, $(NH_4)^+$, $Mg^{+2}$, $Ca^{+2}$, $Ba^{+2}$, $Sr^{+2}$, $Co^{+2}$, $Ni^{+2}$, $Cu^{+2}$, $Zn^{+2}$, $La^{+3}$, $Fe^{+3}$, $Cr^{+3}$, or $Al^{+3}$.

16. The method of claim 14 wherein said fluid is a mixture of alcohol and water.

17. The method of claim 16 wherein said mixture is 70% (volume) isopropyl alcohol and 30% (volume) water.

18. The method of claim 14 wherein said packing is accomplished by centrifuging the sample cell.

19. The method of claim 14 wherein the preselected frequency of measurement is about 1 megahertz.

20. The method of claim 14, further including the step of repeating steps a through e for each sample to be compared.

21. The method of claim 14, wherein the swelling-clay content of the cement mix is determined in accordance with the following relationship:

$$a = \frac{DCM_{cement\ mix} - DCM_{pure\ cement}}{DCM_{pure\ swelling\ clay} - DCM_{pure\ cement}}$$

where:
$DCM_{cement\ mix}$ is the measured dielectric constant of the cement mix sample;
$DCM_{pure\ cement}$ is the measured dielectric constant of the pure cement sample;
$DCM_{pure\ swellable\ clay}$ is the measured dielectric constant of te pure swellable clay sample; and
a is the amount swelling-clay content in the cement mix in a fraction of total weight.

* * * * *